(12) United States Patent
Dvorak et al.

(10) Patent No.: US 8,037,419 B2
(45) Date of Patent: *Oct. 11, 2011

(54) ELECTRONIC SYSTEM FOR COLLECTING AND AUTOMATICALLY POPULATING CLINICAL ORDER INFORMATION

(75) Inventors: Carl Dvorak, Madison, WI (US);
Christopher Alban, Madison, WI (US);
Indu Prakash, Madison, WI (US)

(73) Assignee: Epic Systems Corporation, Verona, WI (US)

( * ) Notice: Subject to any disclaimer, the term of this patent is extended or adjusted under 35 U.S.C. 154(b) by 136 days.

This patent is subject to a terminal disclaimer.

(21) Appl. No.: 12/419,043

(22) Filed: Apr. 6, 2009

(65) Prior Publication Data

US 2009/0307580 A1    Dec. 10, 2009

Related U.S. Application Data

(63) Continuation of application No. 11/286,742, filed on Nov. 22, 2005, now Pat. No. 7,533,353, which is a continuation of application No. 10/013,698, filed on Dec. 10, 2001, now Pat. No. 6,983,423.

(60) Provisional application No. 60/257,971, filed on Dec. 22, 2000.

(51) Int. Cl.
*G06F 3/048* (2006.01)
*G06F 17/30* (2006.01)

(52) U.S. Cl. ........ 715/781; 715/780; 715/708; 715/810; 705/2; 705/3; 128/920

(58) Field of Classification Search ............... 715/700, 715/708, 738, 744, 764, 765, 780, 781, 810, 715/224, 225, 226; 707/1, 100, 200; 705/1, 705/2, 3; 600/300, 301; 128/920
See application file for complete search history.

(56) References Cited

U.S. PATENT DOCUMENTS

2009/0125322 A9 * 5/2009 Dahlin et al. .................. 705/2

* cited by examiner

*Primary Examiner* — Xiomara L Bautista
(74) *Attorney, Agent, or Firm* — Boyle Fredrickson, S.C.

(57) ABSTRACT

A graphical user interface for use on a computer coupled to an enterprise electronic medical records system for accepting order data including an order entry window corresponding to an identified order, the identified order including one or more parameters. The graphical user interface also including an expandable order editing box linked to the order entry window and responsive to identification of the order and adapted to accept an input from a user. The graphical user interface also including an order parameter manager coupled to the enterprise electronic medical records system that is adapted to populate at least one of the one or more order parameters based on information associated with a patient for whom the order is being placed. The graphical user interface further being adapted to display to the user the order and the at least one or more populated order parameters.

20 Claims, 7 Drawing Sheets

ELECTRONIC SYSTEM FOR COLLECTING AND AUTOMATICALLY POPULATING CLINICAL ORDER INFORMATION

CROSS-REFERENCE TO RELATED APPLICATIONS

This patent is a continuation of U.S. application Ser. No. 11/286,742 filed Nov. 22, 2005 now U.S. Pat. No. 7,533,353, which is a continuation of U.S. Pat. No. 6,983,423 filed Dec. 10, 2001 now U.S. Pat. No. 6,983,423, which claims the benefit of U.S. Provisional Patent Application No. 60/257,971, filed Dec. 22, 2000, the disclosures of which are hereby incorporated by reference in their entirety for all purposes.

BACKGROUND OF THE INVENTION

The ability for users to place a wide variety of orders quickly and accurately is vital to the success of an electronic medical records system designed for the acute care setting. If placing electronic orders is too time consuming or involves too much repetitious entry of order parameters, the electronic health care system loses usability and accuracy, which can lower the efficiency of a healthcare enterprise and even compromise the quality of patient care.

Physicians, nurses, clerks, and ancillary staff working in acute care settings must often place a large number of complex orders at once. The care of each patient is likely to require many orders of a number of different types, including medications, blood tests, and nurse interventions. In addition, acute care workflows lead many clinicians to enter orders for multiple patients at the same time after conducting patient rounds, which further increases the need for efficient order entry.

Orders in an acute care setting frequently require the specification of complex order parameters, such as frequency, interval, count, dose, and route, which are a challenge to communicate effectively in any ordering system, even a traditional paper ordering system. A nurse intervention order may tell the nurse to check a patient's vital signs every hour for 24 hours, then to take vitals four times per day for the next two days. Or it may ask that blood levels be tested every two hours until normal levels are reached and then every four hours up to a count of eight times. Electronic ordering systems for both ambulatory and acute care settings have usually relied on the selection of an order from a database, followed by text entry of order parameters on a number of windows for each order before it is filed. In the acute care setting, such entry methods are likely to inhibit regular use of the ordering system or even any use at all, because staff find it too cumbersome to enter order parameters by hand on more than one window for every order.

While these order parameters may be very complex, the likely parameter values for a given order generally belong to a predictable set. In few cases does care require the entry of an order "from scratch" with parameters that cannot be anticipated. A physician is likely to place many orders for patient vitals with similar frequencies at similar intervals. Therefore, text entry of electronic orders not only creates a repetitious workflow that needlessly adds time to the task of order entry, but it fails to take advantage of the ease with which many parameters can be selected from a set of pre-defined common values for the order. In addition, text entry of order parameters increases the likelihood of written error or miscommunication of what are in fact routinely selected values.

BRIEF SUMMARY OF THE INVENTION

According to a preferred embodiment of the invention, a graphical user interface for use on a client computer coupled to an enterprise electronic medical records system for accepting order data is described. The graphical user interface includes an order type navigation bar, wherein order types are selectable from the order type navigation bar. The interface further includes an order entry window, linked to the order type navigation bar, the order entry window responsive to a selected order type to display an order list of the selected order type. The interface yet further includes an expandable order editing box linked to the order entry window and responsive to selection of an order from the order list to provide an order data editing box and an order data summary, the order data summary responsive to the selected order from the order list.

According to another preferred embodiment of the invention, a method of entering order information in a health care setting is described. The method includes the steps of accessing a data repository holding a plurality of possible order templates and a plurality of possible order parameters available for an order, the order corresponding to the order transmittal. The method further includes generating a predictive set of order templates from the plurality of possible order templates available in the database, the predictive set of order templates being substantially smaller than the plurality of possible order templates. The method yet further includes displaying a list of the predictive set of order templates on a graphical user interface and generating, for an order template selected from the predictive set of order templates, a predictive set of order parameters from the plurality of possible order parameters available in the database, the predictive set of order parameters being substantially smaller than the plurality of possible order parameters. The method yet further includes modifying the predictive set of order parameters to include at least one order parameter derived from a record, the record being at least one of a patient record, a user profile, or a preference list and displaying the modified predictive set of order parameters on the graphical user interface.

These particular features and advantages may apply to only some embodiments falling within the claims and thus do not define the scope of the invention.

DETAILED DESCRIPTION OF THE INVENTION

Figure 1:
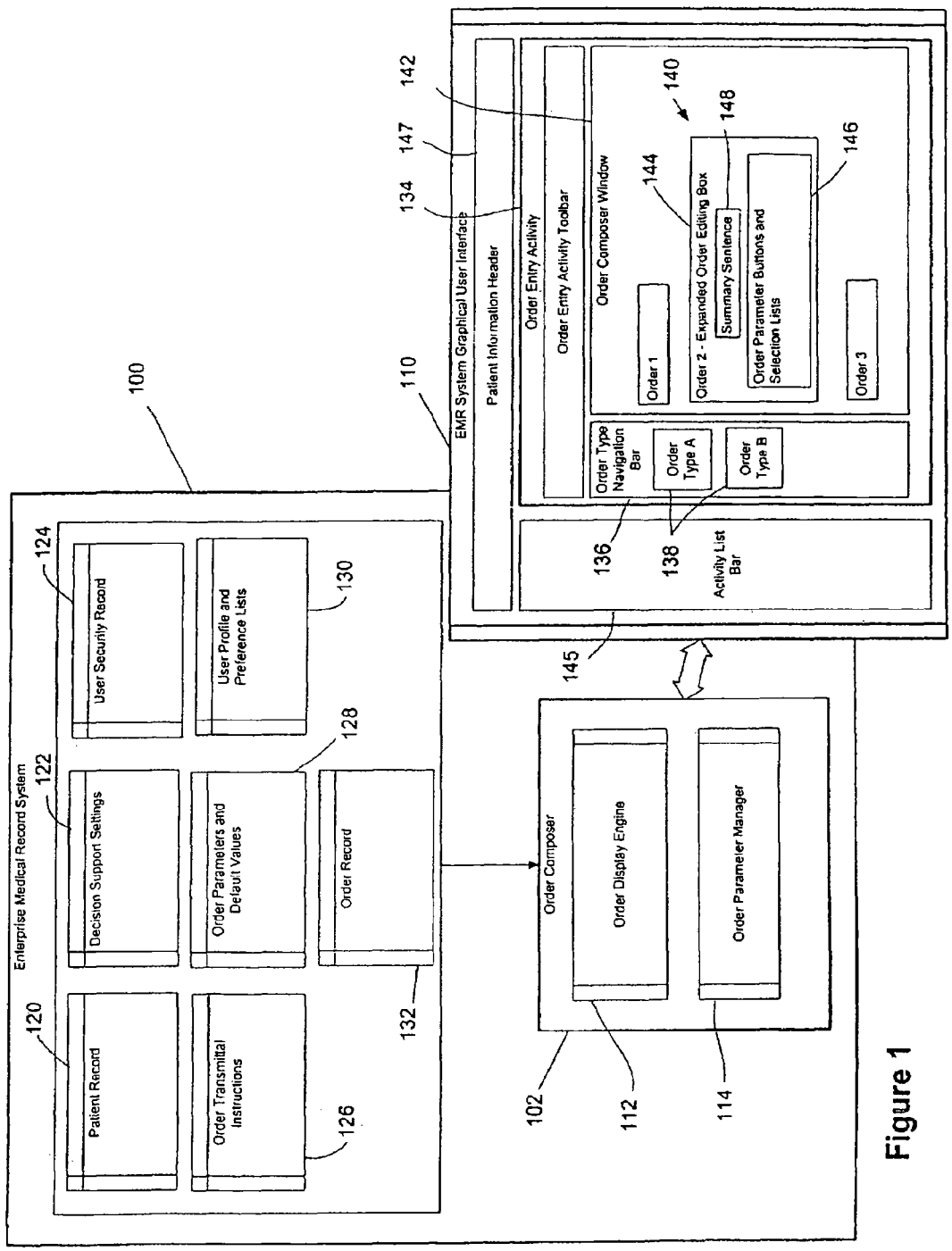
FIG. 1 is a graphical representation of a user interface in accordance with a preferred embodiment of the invention illustrating interaction of the user interface with an electronic medical records (EMR) system.

According to a preferred embodiment of the invention an interactive, graphical user interface presents user-specific lists of orders grouped into types. When the user clicks an order sentence corresponding to that order appears. The user then clicks on the sentence to open an expanded order editing box accompanied by a set of buttons and selection lists encompassing the parameters that must be defined for the order and the most common values for those parameters. To facilitate quick order entry, the entire order entry process can be conducted with the mouse or another pointing device, by selecting the order via a check box and specifying all parameters by clicking buttons and selection lists.

The list of orders, order parameters, and default values can be configured by the users of the enterprise employing apparatus and methods according to preferred embodiments of the invention, in order to reduce the time spent searching for options that are routinely used. Orders can also be grouped and order parameters can be populated by default information on the basis of user preference and history of care for the patient. For example, a user may create order sets containing the orders commonly placed when admitting a patient with a respiratory condition. Alternatively, if a patient has been diagnosed with a specific condition in the past, a system defined order set may appear for the user containing defaults recommended for a patient with the condition.

Order parameters include priority, frequency, dose, route, interval, start and end dates, and count, but they can be extended to include other parameters users want to define for orders. In addition, each order can be configured to contain "condition" buttons, accommodating highly complex order parameters, such as one frequency for an order lasting a specified interval, followed by a different frequency, which lasts for a successive interval. Other condition options can allow users to specify a sequence of orders or to alternate between two orders for specified intervals. As with the order parameters, the condition options are extendible to meet user needs.

As the user selects options for order parameters, the parameter values currently selected appear in a dynamically generated summary sentence at the top of the order editing box. The summary sentence serves several purposes. It clarifies the selections the user has made and shows how the order parameters will appear to the staff member who receives the order. The summary sentence also helps the user keep track of the often complex succession of intervals or conditions selected for the order, in order to reduce the potential for medical error and ensure that the order is properly specified and communicated.

In addition, a variety of decision support alerts can be associated with orders, warning users of factors in patient care that may affect the decision to place the order, such as duplicate orders for the patient or dangerous medication interactions. These decision support options can be configured to locate any important information stored in the enterprise's database repository and present it to the user when the order is selected. Thus, decision support for orders is highly configurable and can provide the user with reports containing procedure instructions, previous order values recorded for the patient, access to clinical reference and enterprise-defined procedure instructions and guidelines for the order, or any other stored information the enterprise wants to present to a user selecting the order.

The user can select as many orders as desired for the patient in one session of use from the single "Order Composer" Window provided. All editing of order parameters can be performed within an expanded order editing box, which appears for each selected order. Only one order editing box is expanded at a time, and when the user clicks another order, the current order's box collapses, saving all the current values and displaying them beside the order in the form of the summary sentence. The user can return to edit any order at any time until the orders for the session are filed. When the desired orders and parameters have been selected, all the order information assembled can be filed simultaneously with a single button click into the database and undergo order transmittal processing. This order transmittal processing can be configured to send order information in a variety of formats to a variety of destinations, including interfaces, faxes, printers, and a comprehensive messaging system that links staff mail boxes, staff worklists, networked terminals, and enterprise mail box pools.

The invention may be implemented as part of an enterprise-wide integrated electronic medical records (EMR) system that is designed to serve large-scale health care enterprises. Therefore, the invention has practical use with the extensive data repositories, network of workstation terminals, and numerous concurrent users employed by such large enterprises.

FIG. 1 represents an overview of the dynamic interaction between the structures of the invention's database repository and the features these structures support in the enterprise medical record (EMR) system 100 including an EMR graphical user interface 110. The EMR System 100 may be implemented using a suitable computing platform including processing, memory and input/output capability. The EMR system 100 may be a standalone system, may be implemented as part of a larger enterprise healthcare information management system, or as part of a network of devices providing information management services to the healthcare enterprise. The EMR System 100 may include two elements of an order composer apparatus 102 according to a preferred embodiment of the invention. These two elements are the order display engine 112 and the order parameter manager 114. The order display engine 112 and the order parameter manager 114 bring together and communicate information stored in various records of the data repository 118 that are relevant to placing clinical orders. These records include the patient record 120, the decision support settings 122, the user security record 124, the order transmittal instructions 126, the order parameters and default values 128, the user profile and preference lists 130, and the order record 132. The order display engine 112 and the order parameter manager 114 present and update the correct information to appear when a specific user employs the EMR graphical user interface 110. The order display engine 112 determines the orders that are listed for each order type based on the user profile and preference lists. It also finds the order parameters to include for each listed order and any default values. Decision support for the listed orders, such as alerts or procedure instructions are also loaded, along with the order transmittal procedures for the session of use. The order display engine 112 also consults the user security record 124 to determine whether the user can file orders or if a cosign or authorization is needed. The order parameter manager 114 stores parameters 146 as the user enters them prior to the filing of orders. These parameters 146 are used to dynamically create the summary sentence 148 for the order.

The EMR graphical user interface 110 presents the user with the order entry activity 134, which is one activity within the larger EMR system 110. The EMR graphical user interface 110 is generated by the order display engine 112, and is displayed to the user via a suitable display device or devices (not shown). The order entry activity 134 contains: an activity list bar 145 listing possible activities that may be undertaken in connection with the current patient, a patient information header 147 that displays identifying and other patient related information about the current patient and an order type navigation bar 136, displaying the list of various order types 138. When the user clicks an order type 138, the list of orders 140 belonging to that order type 138 is displayed in the order composer window 142. When a user clicks an order from the list 140, a sentence statement of the order appears. The user then clicks on the sentence to open an expanded order editing box 144 in the order composer window 142, allowing the user to define all order parameters 146 necessary for the order, as defined by the enterprise employing the invention. The user selects an order from a user-specific list causing the order sentence to appear. By clicking on the sentence, the user then causes the expanded order editing box 144 to appear. Decision support information 122, such as procedure instructions, order alternatives, and formulary options alert the user to import information when the order is selected. When the user has selected all desired orders and parameters, a single button click files the order information assembled in the order composer window 142. The order parameters 146 the user selects for the order appear in the dynamically generated summary sentence 148 at the top of the order editing box 144. All selected orders can be filed simultaneously by clicking the file orders button (not depicted) in the order entry activity toolbar 150.

Figure 2:
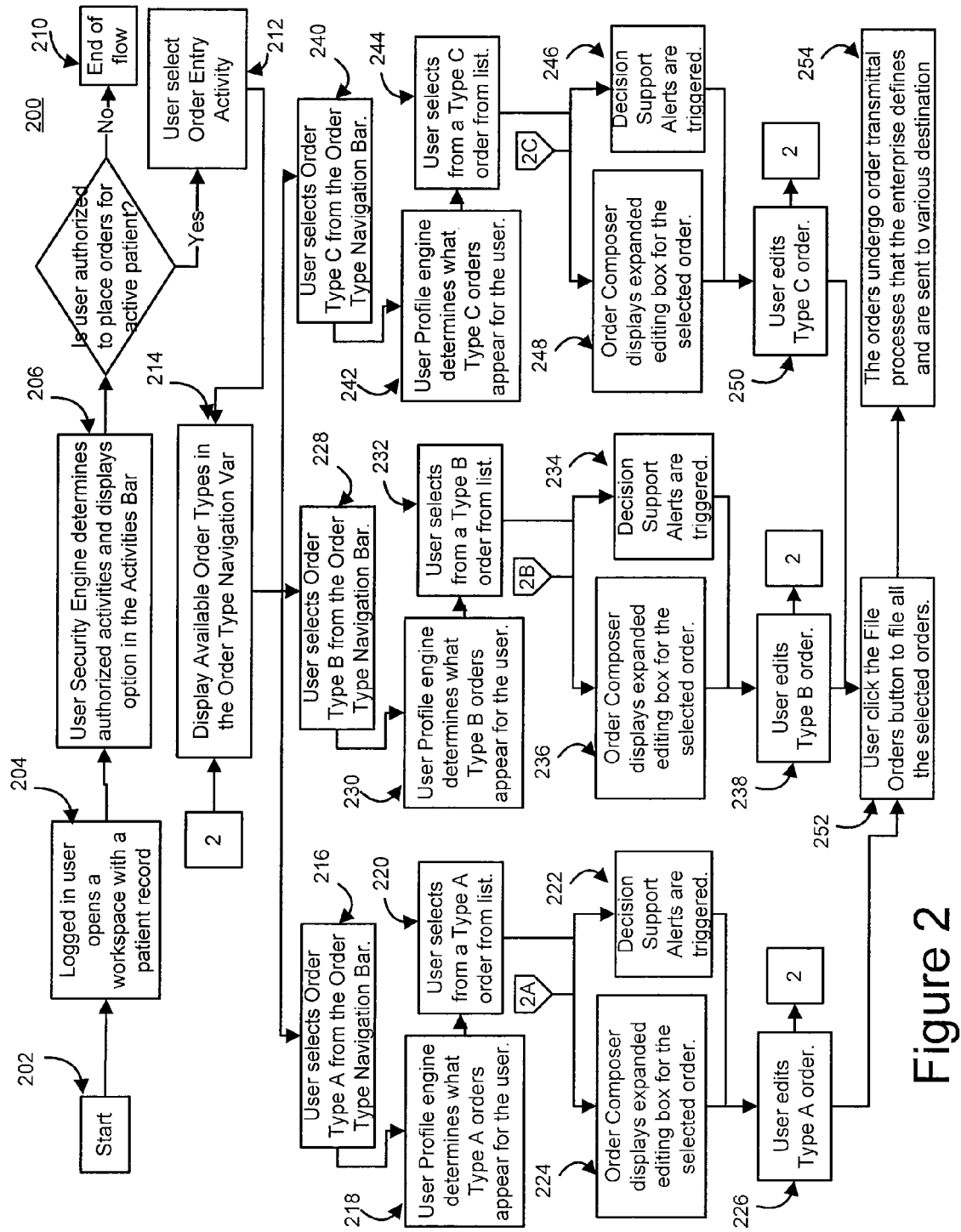
FIG. 2 is a flow chart representation of an order entry workflow in accordance with a preferred embodiment of the invention.

FIG. 2 depicts an order entry workflow 200 in which a user logs into the EMR system 100 supporting the order composer 102, selects three orders of different order types and files them simultaneously. From the start 202, to open the order composer 102, the user must enter a valid login and password 204, and at 206, the EMR system 100 determines the authorized activities for the user and displays options in the activity tool bar 150. The EMR system 100 must also recognize the user as authorized to place electronic orders 208 and 210. Once the user opens 212 the order entry activity 134, the order entry activity 134 displays 214 the available order types 138 to the user in the order type navigation bar 136. Order types can follow clinical categories, but they can also represent order sets based on user preference or enterprise guidelines. As illustrated in FIG. 2, the user proceeds 216 to select Order Type A from the order type navigation bar 136. The user profile engine 130 then determines 218 what orders of Type A appear for the current user. When the user selects 220 the desired order from the Type A list and clicks on the displayed order sentence, two things happen. First, any decision support alerts 122 relevant to the order or its interaction with patient data are triggered and presented 220 to the user. Second, the expanded order editing box 144 appears 224 in the same window in which the order list was displayed, and decision support alerts may also appear in the expanded order editing box 144. Here, the user edits all parameters 146 for the order. The user repeats for Order Type B (228-238) and Order Type C (240-250) the process of selecting an order type and selecting and editing an order. There could be as many more order types to choose from as the enterprise provides and the user creates. Enterprises can add new order types containing any set of orders at any time, and users can define order types that appear only when they use the order entry activity 134. After selecting all desired orders, the user clicks 252 the file orders button and simultaneously files all selected orders, sending them through enterprise-defined order transmittal processes 254.

Figure 3:
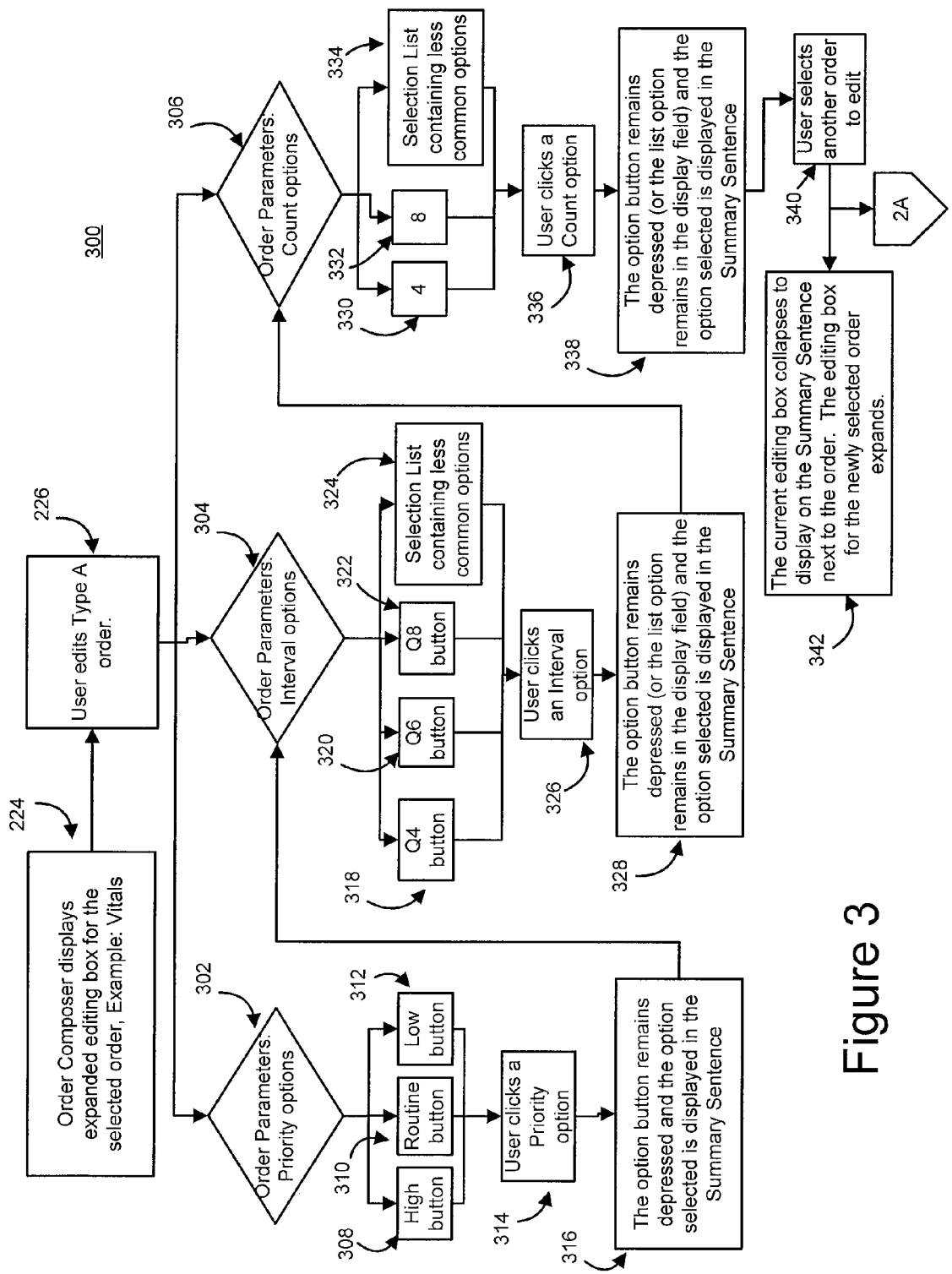
FIG. 3 is a flow chart representation of an order editing workflow in accordance with a preferred embodiment of the invention.

FIG. 3 shows the process 300 of editing 226 a sample Vitals order, which in this scenario was listed in Order Type A selected at step 224 of FIG. 2. The parameters 146 the user sets for the Vitals order are priority 302, interval 304, and count 306. For each parameter, the user can click a pre-defined button, e.g., 308-312 for priority, 318-324 for interval and 330-334 for count, to select a common value for the parameter. In the example illustrated in FIG. 3, the user selects 314, 326 and 336, respectively a High priority 308, a Q4 interval 318, and a count of 4 330. When appropriate, the user can also choose from the more extensive selection list options provided for the interval and count parameters, e.g., buttons 324 and 334. Each time the user sets a value for a parameter 146, the value appears, 316, 328 and 338, in text form as part of the summary sentence 148 at the top of the order editing box 144. The user can change the value selected for a parameter 146 as many times as desired. When the user is done editing the order, the user clicks 340 on the next order to be edited, causing the Vitals order's editing box to collapse 342 and the next order sentence to appear. Clicking on the order sentence causes the editing box for the next order to expand. The parameter values set for the Vitals order appear in the form of the summary sentence 148 next to the order where it appears in the list of Type A orders.

Figure 4:
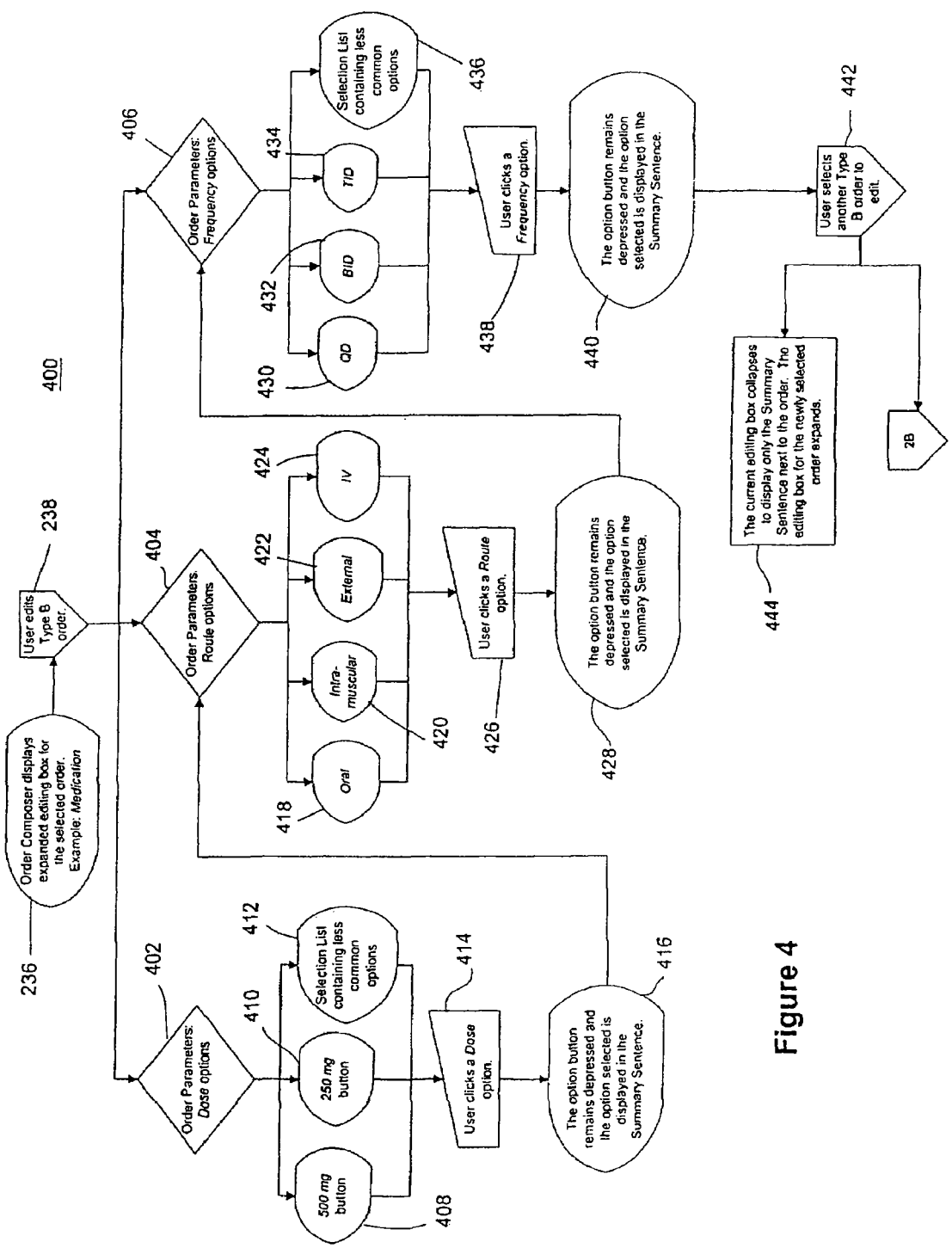
FIG. 4 is a flow chart representation of another order editing workflow in accordance with a preferred embodiment of the invention.

FIG. 4 shows the process 400 of editing 238 a sample Medication order, which in this scenario was listed in Order Type B 236. The parameters 146 the user sets are dose 402, route 404, and frequency 406. For each parameter 146, the user can click a pre-defined button, e.g., 408-412 for dose, 418-424 for route and 430-436 for frequency, to select a common value. In the example illustrated in FIG. 4, the user selects 414, 426 and 438, respectively 500 mg for the dose 408, a route of IV 424, and a frequency of BID (meaning twice per day) 432. The user can also choose from the more extensive selection list options, e.g., buttons 412 and 436, provided for the dose and frequency parameters. Each time the user sets a value for a parameter 146, the value appears, 416, 428 and 440, in text form as part of the summary sentence 148 at the top of the order editing box 144. The user can change the value selected for a parameter as many times as desired. When the user is done editing the order, the user clicks 442 on the next order to be edited, causing the Medication order's editing box to collapse 444 and the order sentence for the next order to appear. Clicking on the order sentence causes the editing box for the next order to expand. The parameter values set for the Medication order appear in the form of the summary sentence 148 next to the order where it appears in the list of Type B orders.

Figure 5:
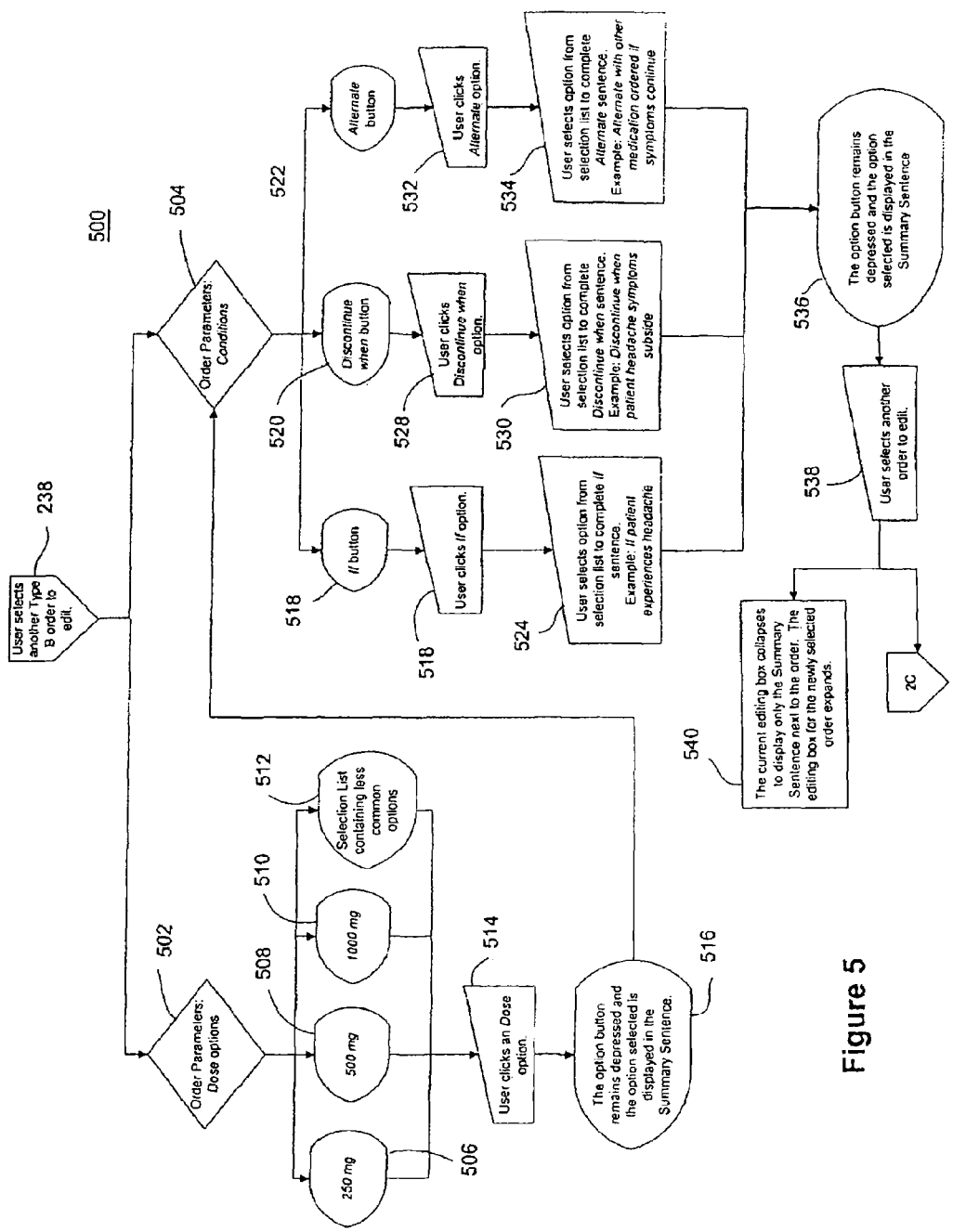
FIG. 5 is a flow chart representation of another order editing workflow in accordance with a preferred embodiment of the invention.

FIG. 5 shows a process 500 for editing 238 another sample Medication order from Order Type B, immediately after editing the Medication order in FIG. 4. The parameters 146 the user sets are dose 502 and condition 504. For each parameter 146, the user can click a pre-defined button, e.g., 506-512 for dose and 518-522 for condition, to select a common value. In the example illustrated in FIG. 5, the user selects 514 and 524, respectively 250 mg for the dose 506 and an If condition 518. The user can also select an option from the more extensive selection list options 512 provided for the dose parameter. When the user selects 524, 528 or 532 a condition 504, the user can choose from an additional selection list of pre-defined text options 526, 530 and 534, respectively in order to complete a sentence explaining the circumstances under which the order should be administered or discontinued. This condition 504 appears 536 along with the other parameter values 516 set for the order in the summary sentence 148 at the top of the order editing box 144. For example, if the user clicks the If condition 518 and chooses patient experiences headache from the selection list 526, the summary sentence 148 would read if patient experiences headache, 500 mg Medication. The user can change the value selected for a parameter 146 as many times as desired. When the user is done editing the order, the user clicks 538 on the next order to be edited, causing the Medication order's editing box to collapse 540 and the order sentence for the next order to appear. Clicking on the order sentence causes the editing box for the next order to expand. The parameter values set for the Medication order appear in the form of the summary sentence 148 next to the order where it appears in the list of Type B orders.

Figure 6:
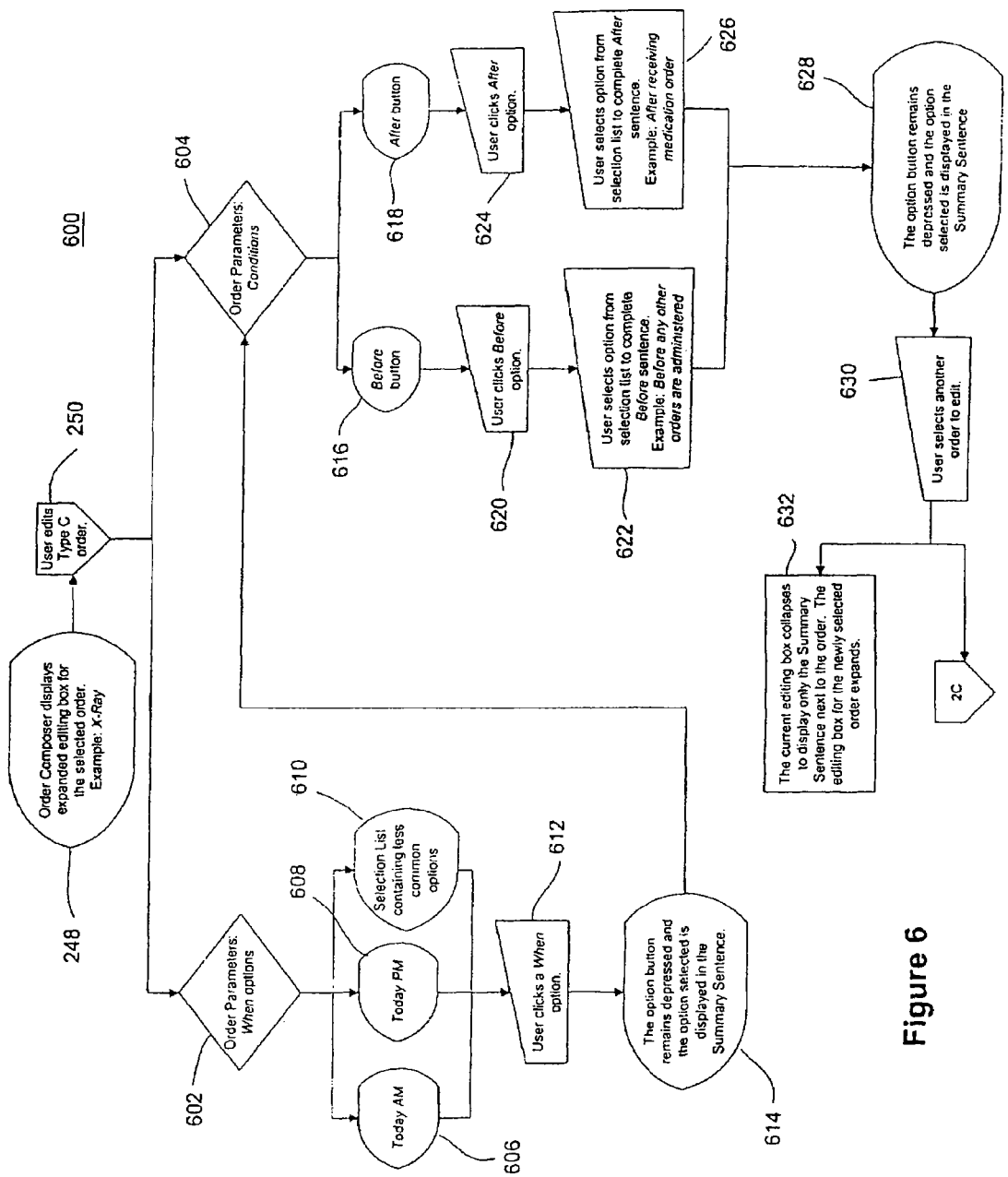
FIG. 6 is a flow chart representation of another order editing workflow in accordance with a preferred embodiment of the invention.

FIG. 6 shows the process 600 of editing a sample X-Ray order, which in this scenario was listed in Order Type C. The parameters 146 the user sets are when 602 and condition 604. For each parameter, the user can click a pre-defined button, e.g., 606-610 for when and 616-618 for condition. In the example illustrated in FIG. 6, the user selects 612 and 620, respectively Today AM for when 606 and a Before condition 616. The user can also choose from the more extensive selection list options 610 provided for the when parameter. Once the user selects a condition 604, the user can choose 622 and 626 from an additional selection list of pre-defined text options in order to complete a summary sentence 148 explaining the sequence in which orders should be administered. This condition 604 appears 614 and 628 along with the other parameter values set for the order in the summary sentence 148 at the top of the order editing box 144. For example, if the user clicks the Before condition button and chooses other orders from the selection list, the summary sentence would read X-Ray before other orders. The user can change the value selected for a parameter 146 as many times as desired. When the user is done editing the order, the user can click 630 on the next order to be edited, causing the X-Ray order's editing box to collapse 632 and the next order sentence to appear. Clicking on the order sentence causes the editing box for the next order to expand. The parameter values set for the X-Ray order appear in the form of the summary sentence (not depicted) next to the order where it appears in the list of Type C orders.

Figure 7:
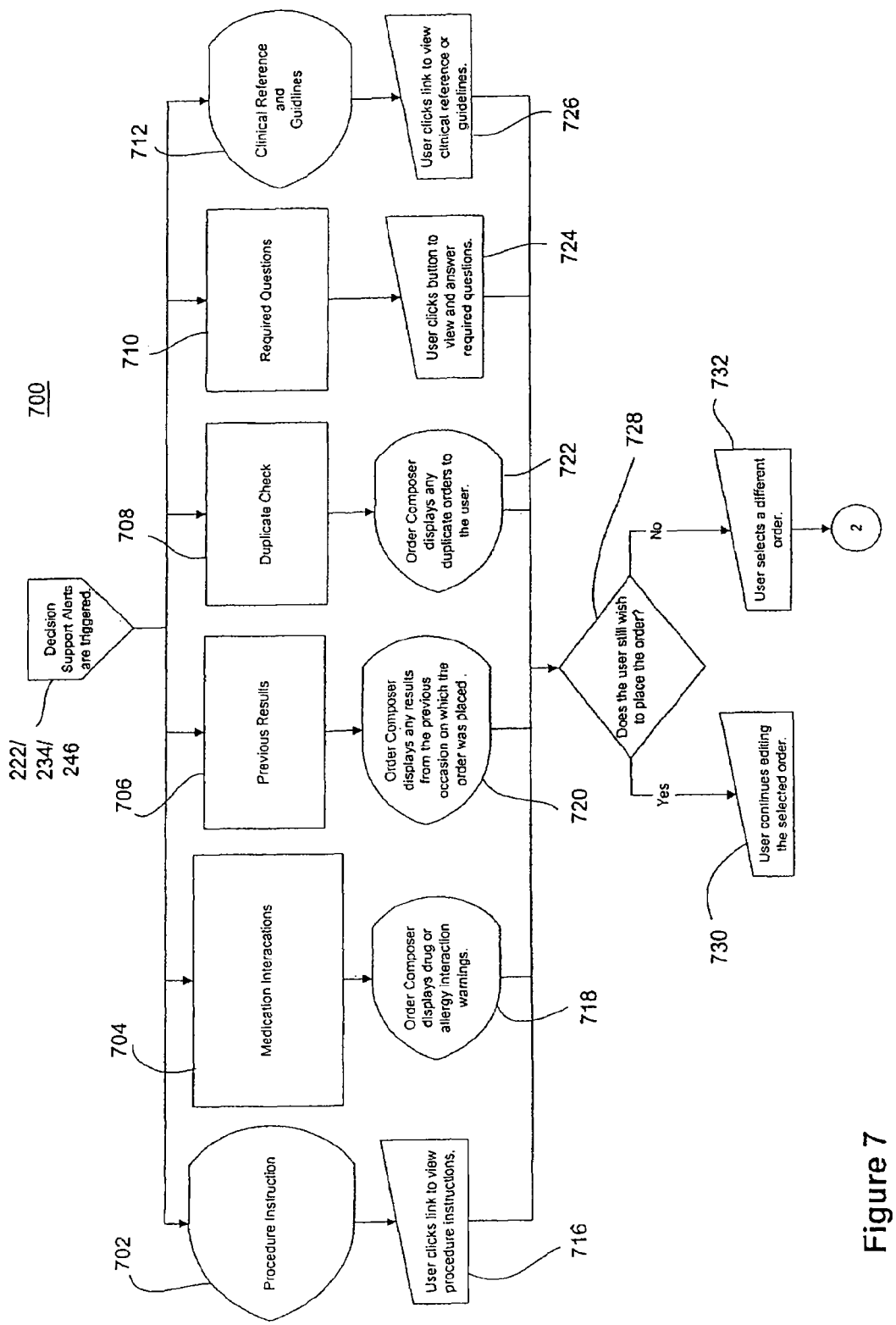
FIG. 7 is a flow chart representation of another order editing workflow in accordance with a preferred embodiment of the invention.

FIG. 7 exhibits the variety of decision support alerts 222, 234 and 246 that may be triggered when a user selects an order to edit. The decision support alerts may be displayed directly within the order editing box, or the decision support alerts may be displayed at an appropriate location with the EMR graphic user interface 110. Any, all, or none of the alerts shown may appear when a user selects the order, depending on how the enterprise employing the invention has configured the decision support settings 122 and the order record 132. Alerts warnings state to the user the type of alert that has been triggered 702-714 and provide access 716-726 to a report or other enterprise-defined information detailing the reason for the alert and/or suggesting alternative orders. There are six alerts depicted as primary examples:

The procedure instructions provide a link to special instructions the enterprise wants a user placing the order to see, 702.

The medication interactions alert the ordering user that the medication order selected may interact dangerously with another medication ordered for the patient or with one of the patient's recorded allergies, 704.

The previous questions warning presents a report to the user displaying previous results the patient has received for the same order, 708.

The duplicate check warns the user if the same order has been placed for the patient within a facility-defined time interval, e.g. 24 hours, indicating that it may be a duplication of the same order, 710.

The required orders alert informs the user that there are questions that must be answered about the order before it can be placed. The user can click a button to view and edit the questions, 712.

The clinical reference and guidelines alert the user that the order may be part of an enterprise protocol that provides specific instructions on a treatment program or that the order is counter-indicated by enterprise protocols. The user can view the guidelines or reference in order to decide whether the order should be placed, 714.

These decision support options can be configured to locate any important information the enterprise employing the invention has stored in its database repository and present it to the user when the order is selected. The user may determine whether the order is to be placed 728 and if so continue editing the selected order 730 or if not select a different order 732.

The invention has been described in terms of several preferred embodiments. It will be appreciated that the invention may otherwise be embodied without departing from the fair scope of the invention defined by the following claims.

We claim:

1. A client computer system coupled to an enterprise electronic medical records system and including a computer-implemented graphical user interface for accepting order data, the graphical user interface comprising:
    an order type navigation bar, wherein order types are selectable from the order type navigation bar;
    an order entry window, linked to the order type navigation bar, the order entry window responsive to a selected order type to display an order list of the selected order type;
    an expandable order editing box linked to the order entry window and responsive to selection of an order from the order list to provide an order data editing box and an order data summary, the order data summary responsive to the selected order from the order list.

2. The graphical user interface of claim 1, wherein the graphical user interface is adapted to retrieve information associated with a patient from a record stored within the enterprise electronic medical records system, the record being at least one of a patient record, a user profile, and a preference list.

3. The graphical user interface of claim 2, wherein the information associated with the patient is retrieved from the patient record, and wherein the order data summary is configured to include at least one of lab information, medication information, vitals, allergy information, procedure information, test information, and a previous order value.

4. The graphical user interface of claim 2, wherein the retrieved information is used to replace a default parameter value.

5. The graphical user interface of claim 1, wherein the graphical user interface is further adapted to populate the order data summary based on the patient's history of care.

6. The graphical user interface of claim 1, wherein the order data summary includes additional information contained within at least one of a patient record, allergy information, lab information, an order record, a user record, a department record, a facility record, and a system record.

7. The graphical user interface of claim 1, further comprising a decision support manager adapted to generate an alert, the alert associated with data stored in the electronic medical records system to aid a user in an order selection process.

8. A computer-implemented method of entering order information in a health care setting, the method comprising:
    providing within a graphical user interface on a first computer, a listing of selectable order types in an order type navigation bar;
    displaying an order list of a selected order type within an order entry window based on selection of an order type;
    displaying an expandable order editing box linked to the order entry window responsive to selection of an order from the order list to provide an order data editing box and an order data summary, the order data summary responsive to a selected order from the order list.

9. The method of claim 8, further including populating the order editing box based on information associated with a patient for whom the clinical order is being placed, the information associated with the patient being stored in a record in a database, the record being at least one of a patient record, a user profile, and a preference list; and displaying at least some of the information associated with a patient for whom the clinical order is being placed in the order data summary.

10. The method of claim 8, further comprising populating order editing box based on one of lab information, medication information, vitals, allergy information, procedure information, test information, and a previous order value.

11. The method of claim 8, further comprising dynamically displaying an order data summary within the display window that is responsive to the identified particular clinical order.

12. The method of claim 11, wherein the order data summary includes additional information contained within at least one of a patient record, allergy information, lab information, an order record, a user record, a department record, a facility record, and a system record.

13. The method of claim 8, further comprising generating a user configurable order type navigation bar listing a plurality of order types.

14. The method of claim 8, further comprising generating an alert, the alert associated with data stored in the database to aid a user in an order selection process.

15. A dynamic order composer device, the order composer device being coupled to and operating in conjunction with an integrated medical record system, the order composer device comprising:

an order type navigation bar, wherein order types are selectable from the order type navigation bar;

an order entry window, linked to the order type navigation bar, the order entry window responsive to a selected order type to display an order list of the selected order type;

an order retrieval system to identify and retrieve from the database repository one or more values for order parameters associated with one or more orders from the order list, wherein the one or more values are associated with a patient for whom the one or more orders are being placed;

an expandable order editing box linked to the order entry window and responsive to selection of an order from the order list to provide an order data editing box and an order data summary, the order data summary responsive to the selected order from the order list; and an order display to display the order data summary.

16. The dynamic order composer device of claim 15, wherein the order retrieval engine is configured to provide a user with the ability to use another user's default values.

17. The dynamic order composer device of claim 15, further comprising an alert engine to generate an alert, the alert associated with data stored in the integrated medical record system to aid a user in an order selection process.

18. The dynamic order composer device of claim 17, wherein the alert engine is further configured to generate a second alert, the second alert associated with patient record data to indicate a specified order is specifically indicated or counter-indicated for a patient.

19. The dynamic order composer device of claim 15, wherein the order retrieval engine is adapted to retrieve at least one of a patient record, a user profile, and a preference list.

20. The dynamic order composer device of claim 15, wherein the order data summary is configured to include at least one of lab information, medication information, vitals, allergy information, procedure information, test information, and a previous order value.

* * * * *